(12) United States Patent
Prinz et al.

(10) Patent No.: US 6,468,809 B1
(45) Date of Patent: Oct. 22, 2002

(54) HIGH EFFICIENCY MAGNETIC SENSOR FOR MAGNETIC PARTICLES

(75) Inventors: Gary A. Prinz, Alexandria, VA (US); Michael M. Miller, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/497,754

(22) Filed: Feb. 4, 2000

(51) Int. Cl.$^7$ ............................................. G01N 33/553
(52) U.S. Cl. .......................... 436/526; 422/50; 422/98; 422/236; 422/276; 436/514; 436/528; 209/214; 210/222; 210/223
(58) Field of Search ............................ 422/50, 98, 236, 422/276; 436/514, 526, 528; 209/214; 210/222, 223

(56) References Cited

U.S. PATENT DOCUMENTS

| | | | |
|---|---|---|---|
| 5,475,304 A | 12/1995 | Prinz | 324/207.21 |
| 5,477,482 A | 12/1995 | Prinz | 365/129 |
| 5,541,868 A | 7/1996 | Prinz | 365/98 |
| 5,661,062 A | 8/1997 | Prinz | 438/3 |
| 5,981,297 A | 11/1999 | Baselt | 436/514 |

*Primary Examiner*—Christopher L. Chin
*Assistant Examiner*—Pensee Do
(74) *Attorney, Agent, or Firm*—John J. Karasek; Stephen T. Hunnius

(57) ABSTRACT

A magnetic sensing element detects the presence of magnetic particles in a binding assay. The magnetic sensing element has at least one planar layer of electrically conductive ferromagnetic material that has an initial state in which the material has a circular magnetic moment within the plane of the layer. The magnetic sensing element has molecules of a first specific binding member attached to it. The device also includes a fluid test medium to which the magnetic sensing element is exposed during the course of a binding assay. The fluid test medium includes magnetizable particles that become immobilized during the assay in relation to the amount of analyte in the test medium. The relative size of the magnetic particle and the magnetic sensing element and the location of the molecules of the first specific binding member on the magnetic sensing element are selected so that when the magnetic particle becomes immobilized with respect to the magnetic sensing element, the radial fringing field of the magnetic particle causes the magnetic moment of at least one layer of electrically conductive ferromagnetic material to shift from circular to radial, thereby causing a detectable change in the electrical resistance of the magnetic sensing element.

28 Claims, 11 Drawing Sheets

HIGH EFFICIENCY MAGNETIC SENSOR FOR MAGNETIC PARTICLES

BACKGROUND OF THE INVENTION

1. Field of the Invention

The present invention relates generally to a sensing device for use in a binding assay for detecting the presence of an analyte and more particularly to a sensing device having a magnetic sensing element that responds to the radial fringing field of a magnetic particle.

2. Description of the Background Art

Binding assays such as immunoassays, DNA hybridization assays, and receptor-based assays are widely used in the medical community as diagnostic tests for a wide range of target molecules or analytes. Binding assays exploit the ability of certain molecules, herein referred to as "specific binding members", to specifically bind target molecules. Specific binding members such as antibodies, strands of polynucleic acids (DNA or RNA) and molecular receptors, are capable of selectively binding to ("recognizing") potential target molecules such as polynucleic acids, enzymes and other proteins, polymers, metal ions, and low molecular weight organic species such as toxins, illicit drugs, and explosives. In a solid phase assay, a recognition event causes binding members in a fluid test medium to become immobilized with respect to a solid substrate in relation to the amount of analyte present in the medium.

Typically, because of the small size of the molecules involved, recognition events in a binding assay cannot be observed directly. This problem is overcome through the use of labeled binding molecules, which indicate their presence through the generation of a measurable signal. Various types of binding assays have been devised that use radioactive, fluorescent, chemiluminescent, or enzymatic labels.

Binding assays that use magnetic particles as labels have been described. Various means have been described for detecting the magnetic particles.

For example, Baselt, D. R. et al, "Biosensor Based on Force Microscope Technology", J. Vac. Sci. Technol. B, vol. 14, no. 2, pp. 789–793, (1996) and U.S. Pat. No. 5,807,758 to Lee et al, incorporated herein by reference, describe a magnetic force sensor called a Force Amplified Biological Sensor (FABS) that uses a cantilever-beam force transducer to measure the total magnetic force exerted by adhering magnetic particles when a magnetic field is applied.

U.S. Pat. Nos. 5,445,970 and 5,445,971 to Rohr, incorporated herein by reference, describe a device that uses a microbalance, rather than a cantilever-beam force transducer, to measure the force exerted by adhering magnetic particles when a magnetic field is applied. Assay methods involving the measurement of force exerted by adhering magnetic particles when a magnetic field is applied are described in U.S. Pat. No. 5,998,224 to Rohr.

R. Kotitz et al. (41$^{st}$ annual conference on Magnetism and Magnetic Materials, November 1996; see abstract book p. 73), incorporated herein by reference, describes a binding assay that uses a Superconducting Quantum Interference Device (SQUID) to detect whether magnetic particles have been immobilized by biological recognition events on the side of a test tube.

U.S. Pat. No. 5,981,297 to Baselt, incorporated herein by reference, describes a binding assay method and apparatus for detecting magnetized particles by monitoring a magnetoresistive or magnetostrictive response of a magnetic field sensor to the magnetized particles.

The orientation of the moment of a magnetizable particle is generally defined by the direction of an external magnetic field applied to the particle. If that field is applied perpendicular to the plane of a magnetic field sensor (in order to avoid affecting the moments in the plane of magnetic layers), the magnetic fringing field from the particle exhibits a circularly symmetric pattern centered on the particle axis. This field contains both radial components in the plane of the sensor and components perpendicular to the plane of the sensor. In the embodiments disclosed in U.S. Pat. No. 5,981,297, the magnetoresistive sensing elements are in the form of thin film magnetoresistive strips. Typically, such magnetoresistive sensing elements have a rectilinear symmetry and uniaxial sensitivity to magnetic fields. These sensing elements respond primarily to perpendicular components of the magnetic fringing field of a magnetic particle and not to the radial components. Thus, the full usefulness of a magnetic particle in generating a detectable signal is not exploited.

SUMMARY OF THE INVENTION

Accordingly, it is an object of this invention to maximize the ability of a magnetic sensing element to detect an attached magnetic particle.

It is another object of the present invention to provide a magnetic sensing element that effectively uses the radial components of the fringing field generated by a magnetized magnetic particle attached to the sensor element to produce a detectable signal.

These and other objects are accomplished by a sensing device that includes a magnetic sensing element that has at least one planar layer of electrically conductive ferromagnetic material that has an initial state in which the material has a circular magnetic moment within the plane of the layer. The magnetic sensing element has molecules of a first specific binding member attached to it. The device also includes a fluid test medium to which the magnetic sensing element is exposed during the course of the assay. The fluid test medium includes magnetizable particles that become immobilized during the assay in relation to the amount of analyte in the test medium. The relative size of the magnetic particle and the magnetic sensing element and the location of the molecules of the first specific binding member on the magnetic sensing element are selected so that when the magnetic particle becomes immobilized with respect to the magnetic sensing element, the radial fringing field of the magnetic particle causes the magnetic moment of at least one layer of electrically conductive ferromagnetic material to shift from circular to radial, thereby causing a detectable change in the electrical resistance of the magnetic sensing element.

The invention further relates a method of detecting an analyte in a test sample using the apparatus described above.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENT

Figure 1:
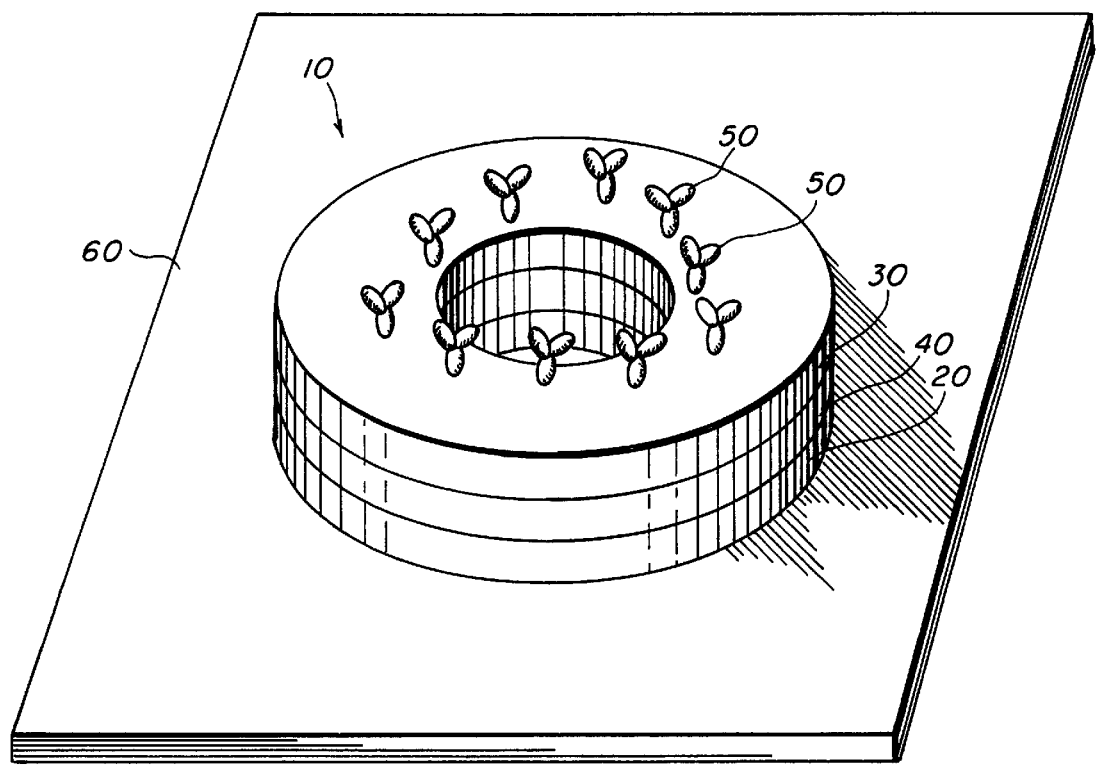
FIG. 1 is a perspective representation of an embodiment of a magnetic sensing element of the present invention having one soft ferromagnetic layer, one nonferromagnetic layer and one hard ferromagnetic layer.

The device of the present invention is intended to be used with any type of solid phase binding assay that involves the use of magnetizable particles as labels and wherein the presence and amount of an analyte can be correlated to the number of magnetizable particles that become immobilized with respect to the surface of the device. The correlation may be a direct (as in, for example, a sandwich assay) or indirect (as in, for example, a competitive assay). The immobilization of the magnetizable particles with respect to the surface of the device may be by direct binding of specific binding members on the magnetizable particles to specific binding members on the surface of the device, or it may be through intermediaries, such as the analyte molecules themselves or other recognition molecules such as secondary antibodies.

The common theme is that the presence and amount of the analyte in the test sample can be related to the number of magnetizable particles that become immobilized on the device by specific binding events. The present invention provides a means to detect whether or not magnetizable particles have become immobilized.

As used herein, the term "specific binding member" refers to a molecule that specifically binds to the another molecule through chemical or physical means. Typically, the term "specific binding member" refers to a member of a binding pair such as antigen-antibody binding pairs. Other binding pairs include, but are not intended to be limited to, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), sugar and boronic acid, and similar molecules having an affinity which permits their association in a binding assay. A binding member may also be made by recombinant techniques or molecular engineering. If the binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other binding members. The details of the preparation of such antibodies, peptides and nucleotides and their suitability for use as binding members in a binding assay are well-known to those skilled-in-the-art. A binding member may also be part of a cell, virus or other biological entity that is immobilized on a surface or on a particle.

As used herein, the term "first binding member" refers to a binding member that is attached to the surface of the magnetic sensing element and the term "second binding member" refers to a binding member that is attached to a particle. As stated above, the device of the present invention may used with assays of a type wherein binding events take place through intermediate molecules. Therefore, it is not a requirement in the definition of "first specific binding member" and "second specific binding member" that the first specific binding member and the second specific binding member bind directly with each other.

Throughout the specification and the claims that follow, it should be understood the terms "upper", "lower", "top" and "bottom" are used as terms of convenience to distinguish various surfaces and layers relative to each other and relative to the substrate on which the layers are constructed. Neither "upper", "lower", "top" or "bottom", as used in the specification and claims that follow, imply the orientation of any element with respect to the gravitational field. Likewise, the terms "clockwise" and "counterclockwise" are used as terms of convenience to distinguish rotational directions relative to each other.

The terms "magnetically hard material" and "magnetically soft material" are used herein as they typically are used in the field of magnetoresistive devices. In particular, the term "magnetically hard material" refers to a material that has a magnetic moment that requires a significantly greater magnetic field strength to reorient than is required to reorient the magnetic moment of a magnetically soft material. Materials ordinarily classified as magnetically hard or magnetically soft materials are generally useful for those purposes in the present invention. Additionally, an antiferromagnetic layer can pin the magnetic moment of an overlayer ferromagnetic layer, thus rendering the pinned ferromagnetic layer a magnetically hard layer within the meaning of the present specification and claims. Furthermore, layers using identical materials can be made to be hard or soft relative to one another merely by utilizing different thicknesses.

As used herein, the terms "magnetizable particle", "magnetic particle" and "magnetized particle" are used interchangeably to refer to an already magnetized particle or to a particle that can be readily magnetized by the application of a magnetic field.

As used herein, the terms "ring" and "circular" mean a closed loop. While a ring is preferably in the shape of a circular washer, other shapes that can accommodate a closed loop, such as elliptical, oval, square, cylindrical, etc. are permissible The magnetic sensing element of the present invention includes at least one planar layer of electrically conductive ferromagnetic material having an initial state in which the material has a circular magnetic moment within the plane of the layer. In the operation of the device of the invention, when a magnetized particle becomes immobilized or attached to the magnetic sensing element, the radial fringing field of the magnetic particle interacts with the magnetic sensing element and causes the magnetic moment of the planar layer to shift from circular to radial. This causes a change in the electrical resistance of the element, which can be measured as a change in current or voltage through the device. As discussed below, several different embodiments based on this principle can be described. In most embodiments, the change in resistance occurs due to the spin-valve effect, which is described, for example, in U.S. Pat. No. 5,477,482, to Prinz (see FIG. 18 of that patent) and U.S. Pat. No. 5,541,868 to Prinz, both incorporated herein by reference. U.S. Pat. No. 5,541,868 describes non-volatile ferromagnetic random access memory elements comprising magnetic stacks of rings of hard ferromagnetic materials alternating with rings of magnetically soft materials. The magnetic stacks described in Prinz '868 patent may be adapted for use as the magnetic sensing element of the present invention.

A typical magnetic sensing element is depicted in FIG. 1. The magnetic sensing element 10 includes a stack of two ferromagnetic rings- a bottom ring 20, typically of hard ferromagnetic material, that rests on a solid surface 60 and a top ring 30, typically of soft ferromagnetic material that has molecules 50 of a first binding member attached to it. A nonferromagnetic ring 40 separates the top and bottom ferromagnetic rings. The rings are all stacked like a set of washers and each ring is in electrical contact with the adjacent ring. The magnetic sensing element may also include a passivation layer (not shown) over the top ring. (For clarity of illustration, the electrical leads that allow the detection of changes in magnetoresistance are not shown.) The present invention is not limited to configurations wherein the hard ferromagnetic layer is the bottom layer and the soft ferromagnetic layer is the top layer. The order of the layers may be reversed.

Figure 2:
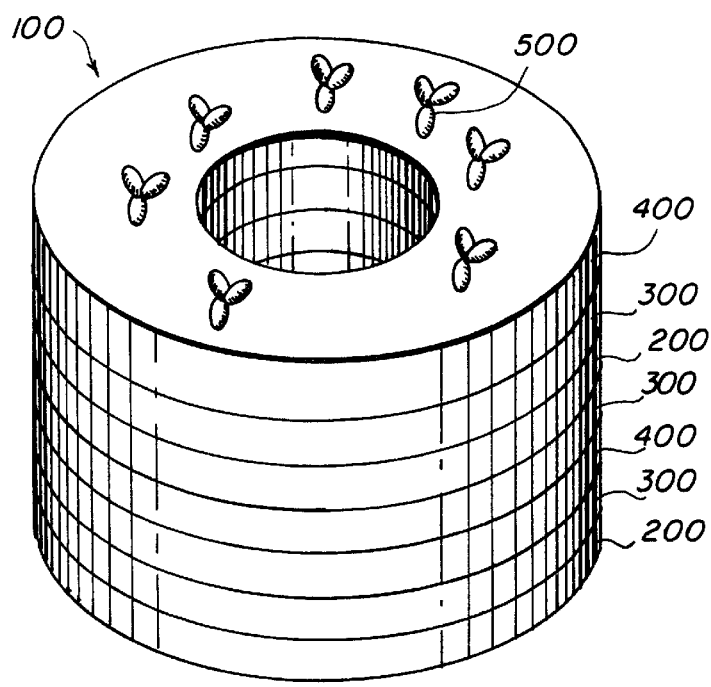
FIG. 2 is a perspective representation of an embodiment of the magnetic sensing element of the present invention having more that one soft ferromagnetic layer, more that one hard ferromagnetic layer and more than one nonferromagnetic layer.

The sensor element may have more than one hard layer and more than one soft ferromagnetic layer. Such an structure is shown in FIG. 2, wherein the magnetic sensing element 100, has layers of hard ferromagnetic rings 200 and soft ferromagnetic rings 300, separated by nonmagnetic conductive or insulative layers nonferromagnetic rings 400. The magnetic sensing element has molecules 500 of the first binding member attached to the top-most layer. (The magnetic sensing element may also include a passivation layer (not shown) over the top ring.) In multilayer stacks, hard layers are generally alternated with softer ferromagnetic layers. (For clarity of illustration, the electrical leads that allow the detection of changes in magnetoresistance are not shown.) The present invention is not limited to the exact configurations shown. The number of layers may be greater or lesser than what is illustrated, and the order of soft and hard layers may be reversed.

In a typical device of the present invention, a magnetically hard ferromagnetic layer has a fixed magnetic state in the form of a closed magnetic circuit whose moment is oriented either clockwise or counterclockwise around the center of the layer. A softer ferromagnetic layer has a closed magnetic circuit whose moment, in the initial or resting state, is oriented either parallel or anti-parallel to the magnetic moment of the magnetically hard layer, either clockwise or counterclockwise around the magnetically soft layer. When there is more than one hard layer and more than one soft layer, all the hard layers will have magnetic moments oriented in the same direction as each other, clockwise or counterclockwise, and all the soft layers will have their magnetic moments oriented in the same direction as each other, clockwise or counterclockwise. When a voltage is applied across the device, the resistance through the device depends upon whether the magnetic moments of the hard ferromagnetic layers are aligned in the same direction or the opposite direction with respect to the soft ferromagnetic layers. Resistance to current flow is higher when their magnetic moments are not aligned in the same direction, i.e, anti-parallel (anti-aligned). The resistance to current flow is lower when their magnetic moments are aligned in essentially the same direction (parallel). Resistance to current flow is an intermediate amount when the magnetic moments are neither parallel nor anti-parallel, such as when one layer has a circular magnetic moment and the other layer has a radial magnetic moment. As discussed below, the alignment of the magnetic moment of a soft layer of the device is affected by the radial magnetic field produced by a magnetic particle.

Figure 3:
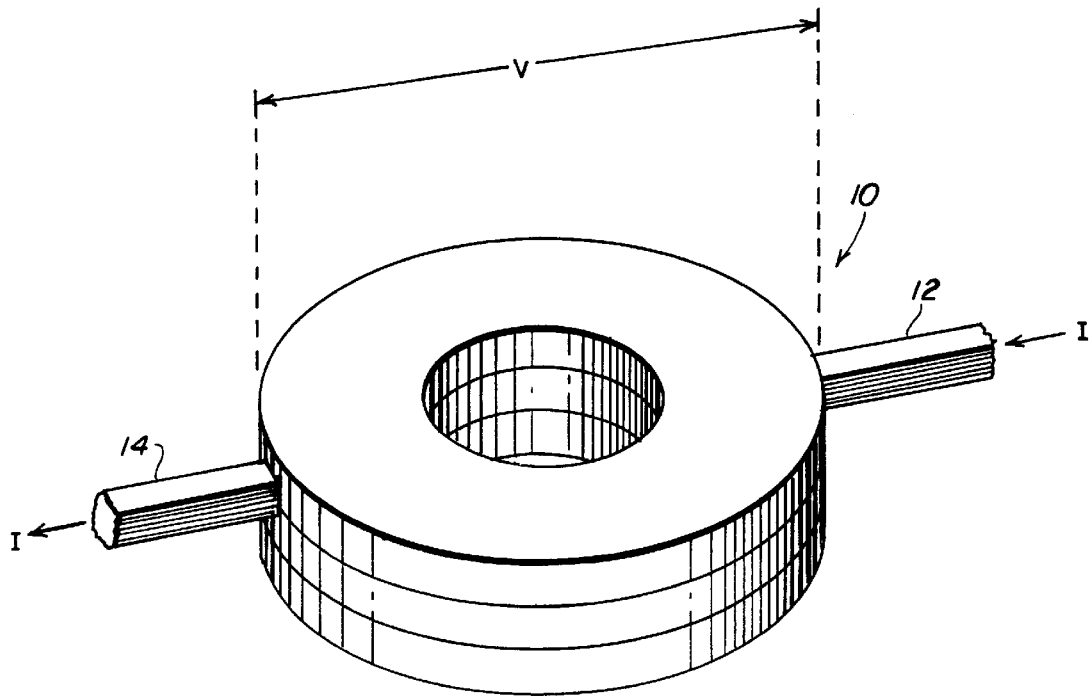
FIG. 3 is a perspective representation of the magnetic sensing element in an embodiment that has electrical current leads in a current-in-plane (CIP) configuration.
Figure 4:
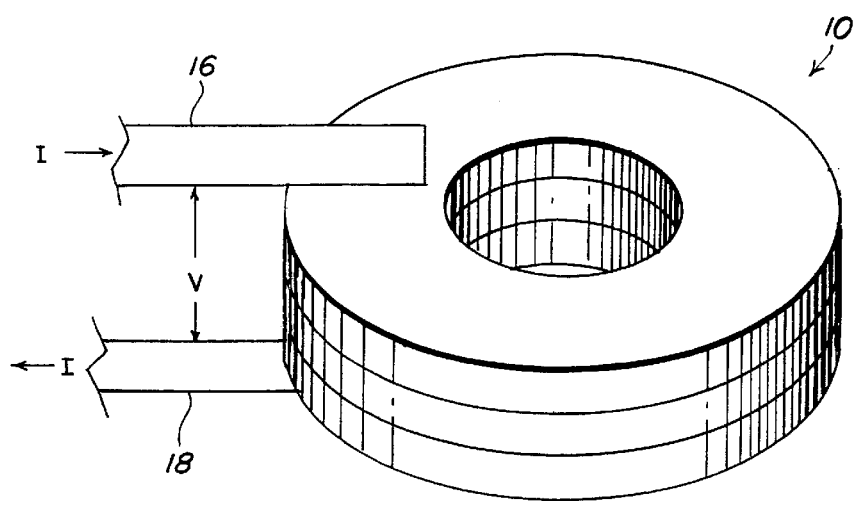
FIG. 4 is a perspective representation of the magnetic sensing element in an embodiment that has electrical current leads in a current-perpendicular-to-plane (CPP) configuration.

The resistance of a device may be measured in either a current-in-plane (CIP) configuration or a current-perpendicular-to-plane (CPP) configuration. FIG. 3 represents the CIP configuration wherein electrical leads 12 and 14 are connected to the device 10 so that an electrical current is passed across the longitudinal axis of the device, parallel to the planes of the device.(For clarity of illustration, the molecules of the first binding member are not shown.) The resistance of the device is then determined by the voltage drop between the electrical terminals at the two sides of the device. FIG. 4 represents the CPP configuration wherein electrical leads 16 and 18 are connected to the device 10 so that an electrical current is passed through terminals on the top and bottom of the stack, perpendicular to the planes of the device. (For clarity of illustration, the molecules of the first binding member are not shown.) Again, the resistance of the device is then determined by the voltage drop between the electrical terminals at the top and bottom of the device.

In a typical device of the present invention, relative size of the magnetizable particles and the magnetic sensing element, and the location of the first binding member on the magnetic sensing element are selected so that when a magnetic particle becomes attached to the magnetic sensing element, the radial field of the magnetic particle is able to cause the magnetic moment at least one layer of electrically conductive ferromagnetic material to shift from circular to radial.

Typically, the molecules of the first binding member are located in a top central region of the magnetic sensing element so that when a magnetic particle becomes bound to the magnetic sensing element, it does so in a region that is co-axial with the centers of the circular magnetic moments of the ferromagnetic layers. This allows the radial fringing field of the particle to interact with the layers of electrically conductive ferromagnetic material in all directions.

Figure 5:
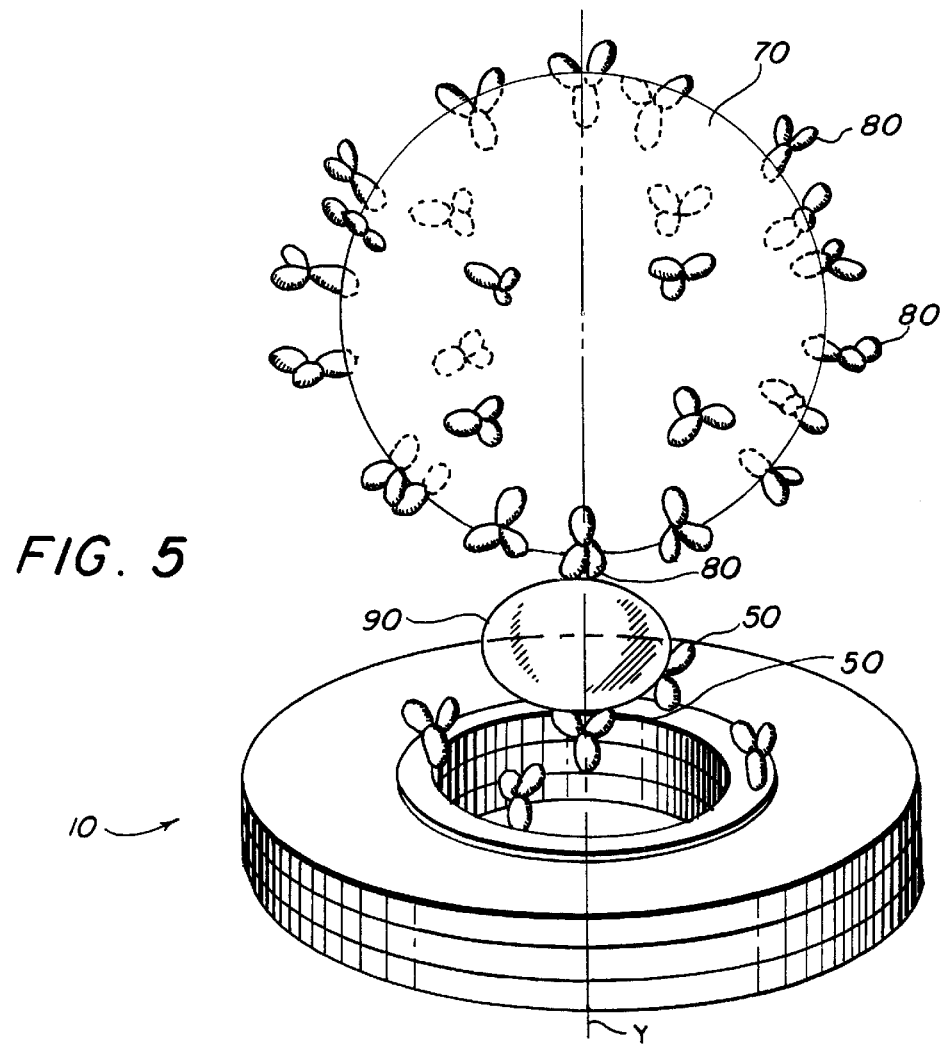
FIG. 5 is a perspective representation of the magnetic sensing device during a typical binding assay.

FIG. 5 is a perspective representation of the magnetic sensing device during a typical binding assay known as the "sandwich assay". An analyte molecule 90 binds to the top of the magnetic sensing device 10 by way of molecules 50 of the first binding member. A magnetic particle 70 that is coated with molecules 80 of the second binding member binds to the analyte so that the particle is immobilized in a central position with respect to the magnetic sensing device. (In this instance, the first binding member and second binding members are antibodies to the analyte.) Since the molecules 50 of the first binding member are located around the top center portion of the magnetic sensing element so that they bind the analyte from every side, the magnetic particle is held approximately at a point along an axis Y that is perpendicular plane of the layer and passes through the center of the circular magnetic moment. (For clarity of illustration, electrical leads are not shown.)

Figure 6:
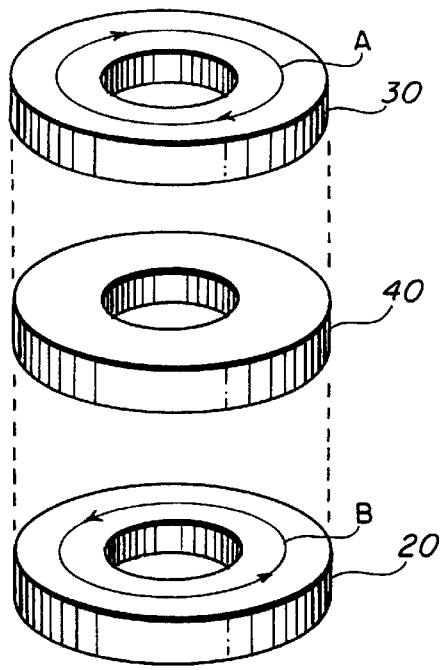
FIG. 6 is an exploded perspective view of a typical three-layer element showing the magnetic moments of the respective layers.
Figure 7:
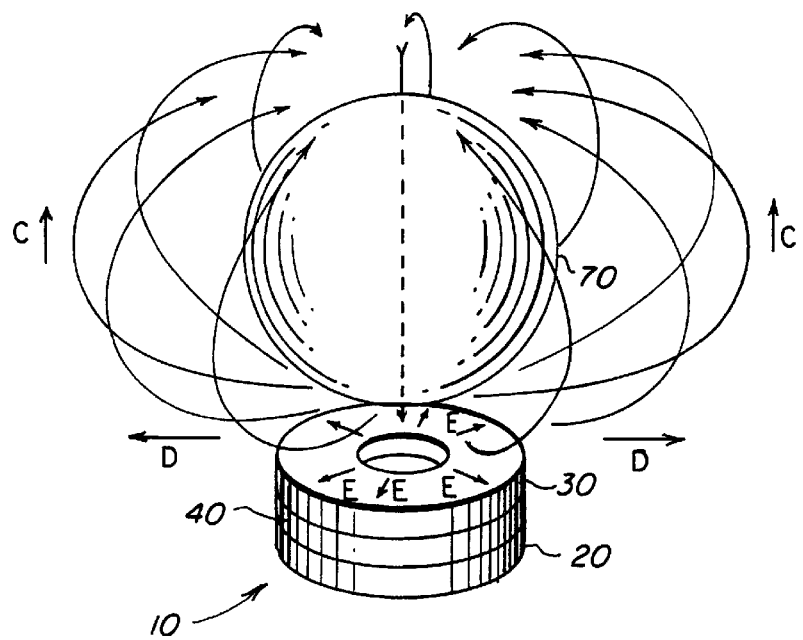
FIG. 7 is a representation of how the magnetization of a typical magnetic sensing element is affected by the immobilization of a magnetic particle on the device.

The details of how a magnetic particle affects the magnetic configuration of these sensors follows below. FIG. 6 is an exploded perspective view of a typical three-layer device made up of a bottom layer 20 of hard magnetic material having a counterclockwise circular magnetic moment (shown by arrow A), a middle layer 40 of nonferromagnetic material, and a top layer 30 of soft magnetic material having a clockwise circular magnetic moment (shown by arrow B). (The relative position of the hard and soft layers can be reversed, with the hard layer as the top layer and the soft layer as the bottom layer.) (For clarity of illustration, the electrical leads and molecules of the first binding member are not shown.) Because the alignment of the magnetic moments of the layers is anti-parallel, such a device has a relatively high electrical resistance. FIG. 7 is a representation of how the magnetic moment of the soft layer is affected by the immobilization of a magnetic particle on the device. The magnetic sensing element 10 is represented by a soft layer, 30, a nonferromagnetic layer 40 and a hard layer 20. The magnetic fringing field of the particle 70 has a perpendicular component (shown by arrows C) and a radial component (shown by arrows D). The radial field interacts with the soft layer 30, causing the magnetic moment (shown by arrows E) of this layer to become radial, while leaving the hard layer 20 unaffected. As a result, the layers are no longer antiparallel and the electrical resistance of the device is lowered. If, in the original configuration, the hard layer and the soft layer had had a parallel alignment of magnetic moments, the effect of the shift of the magnetic moment of the soft layer from circular to radial would be to increase the electrical resistance through the device. (For clarity of illustration, the electrical leads and molecules of the first binding member and the molecules of the second binding member are not shown.)

Figure 8:
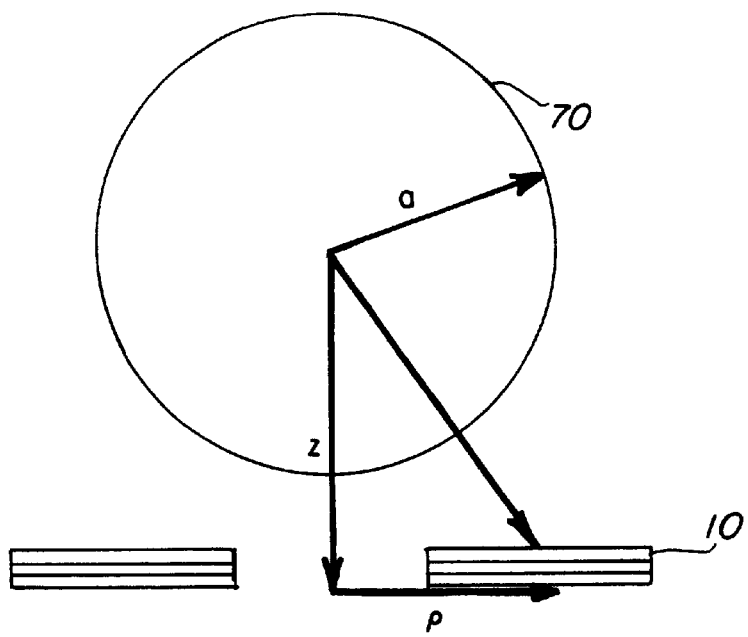
FIG. 8 is a diagrammatical, cross-sectional side representation of a magnetic particle immobilized on a magnetic sensing element.

The following considerations may be taken into account in selecting the dimensions of the magnetic sensing element: A uniformly magnetized sphere exhibits a purely dipolar magnetic field given by:

$$\vec{B}(\vec{r}) = \frac{3\hat{r}(\hat{r} \cdot \vec{m}) - \vec{m}}{r^3} \quad (1)$$

where $\vec{m}$ is the magnetic moment of the magnetized sphere and r is the distance from the center of the sphere. The magnetic field used to align the magnetic moments in the soft magnetic layers of the magnetic sensing element is directed radially within the plane of the device. The relevant geometry used in the equations below is shown in FIG. 8, which is a cross-sectional representation of a magnetic particle 70 of radius a immobilized on a magnetic sensing element 10. (For clarity of illustration, the electrical leads and molecules of the first binding member and the molecules of the second binding member are not shown.) The magnetic moment m of the particle is directed along z. The radial component of the magnetic field has a form given by $$B_p = \frac{3mz\rho}{r^5} \quad (2)$$

where $$r = \sqrt{z^2 + \rho^2} \quad (3)$$

The maximum component of B will be in a circle in a plane perpendicular to the moment such that:

$$\rho_{max} = \frac{z}{2} \quad (4)$$

For a bead with radius a, the maximum field in the plane tangent to the bead will be at =a/2. The most efficient configuration in general is for an annular ring sensor with an average radius of approximately z/2, where z is determined by the radius of the bead plus any "standoff" distance the bead may have from the sensor. This standoff distance is due to any passivation layers that may overlay the sensor. For example, if for a bead of radius a and a passivation layer of thickness t, the optimal average radius of the sensor is $$\bar{\rho} = \frac{a+t}{2} \quad (5)$$

Figure 9:
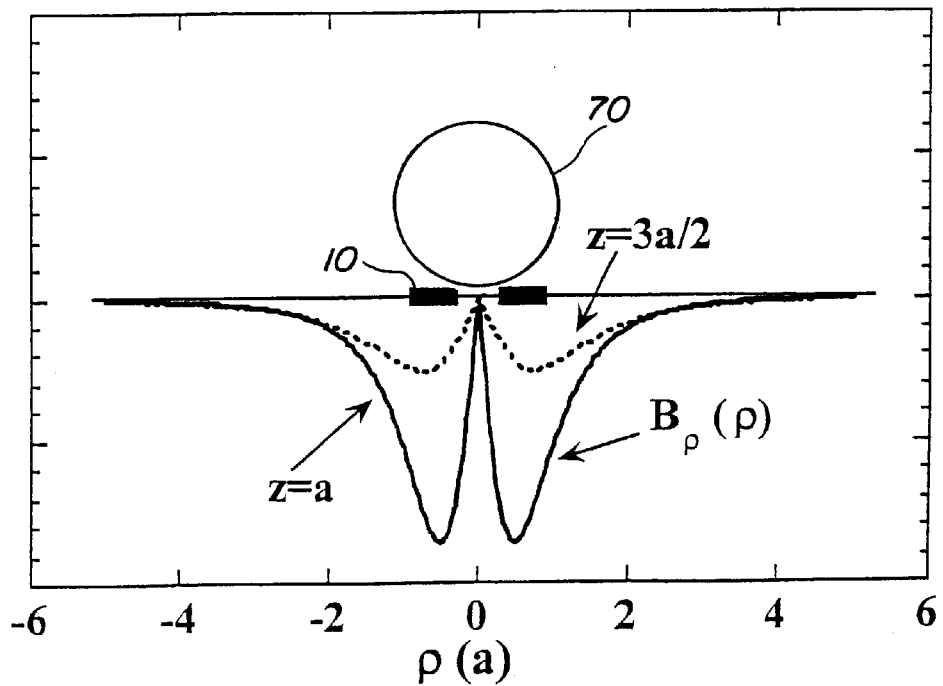
FIG. 9 is a superimposed cross-sectional side view of a magnetic particle immobilized on a magnetic sensing element and a graphic representation of the dependence of $B_\rho$ on the standoff distance z (in units of bead radius) as a function of the radial distance $\rho$.

Ideally, the inner and outer radii of the ring will be as close to the average radius as possible. However, the ring will require a finite width and, therefore, the specific width will be engineered to some value such that the magnetic field is within, say, 80% of the maximum value. The details of these dimensions will be a function of magnetic particle material and size, stand-off distance, and the magnetic and non-magnetic materials and layer thicknesses in the sensor. FIG. 9 is a graphic representation of the dependence of $B_\rho$ on the standoff distance z (in units of bead radius) as a function of the radial distance ρ.

The embodiments of the present invention described herein vary in the number and types of magnetic layers, in the ways in which various layers of the magnetic sensing element react to the presence of a radial fringing field and in the ways in which a change in magnetoresistance is detected. In each instance, the embodiments may be readily constructed using existing lithographic techniques.

Figure 10A:
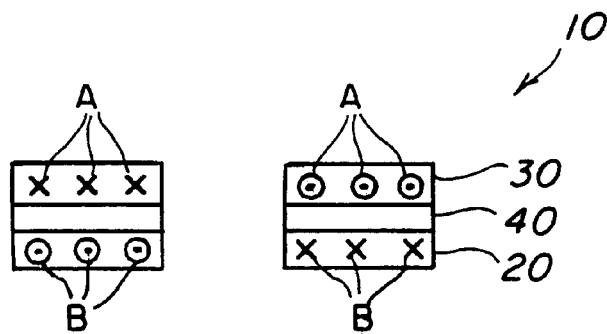
FIGS. 10a and 10b are side cross-sectional views of a magnetic sensing element of the first embodiment, without and with an immobilized magnetic particle.
Figure 10B:
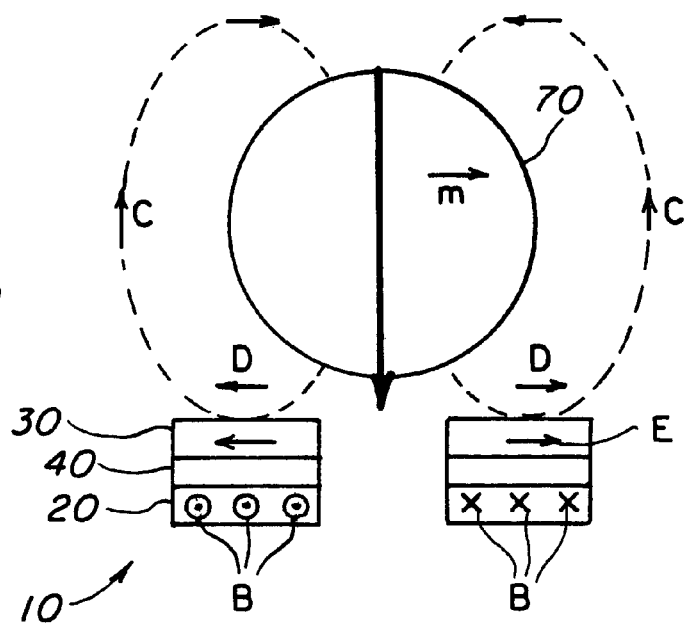
Figure 11:
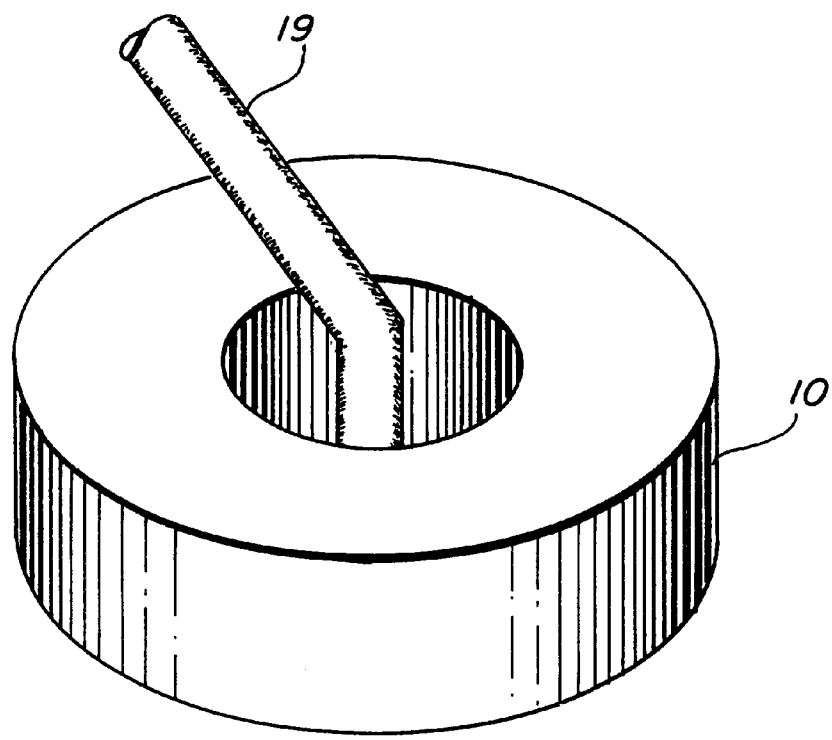
FIG. 11 is a perspective representation of a magnetic sensing element with an auxiliary current carrying wire.

The first embodiment, which has already been described above and illustrated in FIGS. 1, 2, 6 and 7, is a giant magnetoresistive (GMR) device that uses the radial magnetic field of the particle to rotate the moment of a soft layer or layers from a circumferential orientation to a radial orientation. This embodiment includes a hard layer or layers that have a magnetic moment that remains fixed. The resistance of this element either increases or decreases by depending upon whether the original orientation of the hard and soft layers were originally parallel or anti-parallel. The effect of a magnetic particle is then to change the state of the sensing element from either a low or high resistive state (parallel or anti-parallel) to a state of intermediate resistance—a 90° orientation between the hard and soft layer moments. This embodiment is referred to as the "half-scissors" mode. This embodiment is further illustrated in FIGS. 10a and 10b, which are a cross-sectional views of a magnetic sensing element 10 without and with an immobilized magnetic particle. (For clarity of illustration, the electrical leads and molecules of the first binding member and the molecules of the second binding member are not shown.) In the drawings, x represents the portion of the circular magnetic moment pointing into the page, and Θ represents the portion of the circular magnetic moment pointing out of the page. As depicted in FIG. 10a, in the absence of an immobilized particle, the magnetic moment A of the soft layer 30 is clockwise and the magnetic moment B of the hard layer 20 is counterclockwise. As depicted in FIG. 10b, in the presence of an immobilized particle 70 having a magnetic fringing field with a perpendicular component C and a radial component D, the magnetic moment of the soft layer 30 becomes radial, as indicated by arrow E. For the measurement of resistance, this embodiment can have either a current-in-plane (CIP) configuration or a current-perpendicular to plane (CPP) configuration. In this embodiment, the initial state of the alternating layers can be either anti-parallel (as illustrated) or parallel. The layers can be made to be anti-parallel by selecting the thickness of the conducting spacer layer to anti-ferromagnetically couple alternating magnetic layers by way of exchange coupling, as described in S.S.P. Parkin, "Systematic Variation of the Strength and Oscillation Period of Indirect Magnetic Exchange Coupling through the 3d, 4d, and 5d Transition Metals", Physical Review Letters 67, 3598(1991), incorporated herein by reference. However, in some sense, the initial state is arbitrary since this embodiment relies on a net change in resistance due to the rotation of the soft layer only. Additionally, the circumferential orientation of some or all of the ferromagnetic layers can be controlled or set using an auxiliary current-carrying wire that is coaxial with the ring. FIG. 11 is a representation of a device of the present invention having an auxiliary current-carrying wire 19 that is coaxial with the rings of the device Such a wire passes through the central portion of the device and is electrically isolated from the ferromagnetic rings. The current in this wire produces a circumferential magnetic field. (For clarity of illustration, the electrical leads and molecules of the first binding member and the molecules of the second binding member are not shown.) A similar structure is described to Prinz '868, cited above. Alternatively, an auxiliary current can be passed directly though the stack of layers, perpendicular to the layers, as described in Prinz '898.

Figure 12A:
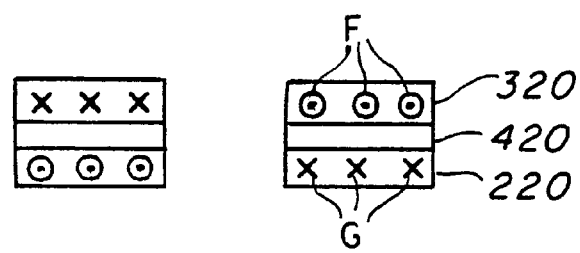
FIGS. 12a and 12b are side cross-sectional views of a magnetic sensing element of the third embodiment, without and with an immobilized magnetic particle.
Figure 12B:
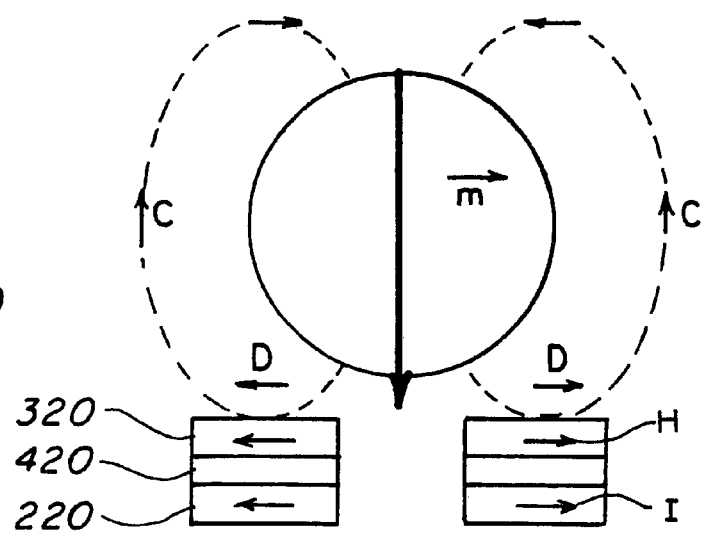

The second embodiment, also a giant magnetoresistive (GMR) device, uses the above described structure with the additional effect described Prinz '868 in which an electrical current passing through the ring stack causes the soft layer magnetization to reverse. The radial magnetic field of the magnetic particle coupled with this current induced reversal allows for a threshold to be set by either the current or the particle field and for the threshold to be crossed by either the particle field or the current. The effect of the magnetic field from the particle is to rotate the soft layer moment to a radial orientation. A current sent through either the ring, a coaxial current lead (see above) or combination thereof will then counter-rotate the moments in the soft layer(s) relative to the original orientation. With a bead present providing an additional "boost", the element is then made to "latch" in a high or low state. This embodiment can also have either a current-in-plane (CIP) configuration or a current-perpendicular to plane (CPP) configuraion A third embodiment, also a giant magnetoresistive (GMR) device, comprises two or more magnetic layers having identical or nearly identical coercivities (such as, for example, two or more magnetically soft layers), the layers being separated by a non-magnetic conducting spacers. By proper selection of the spacer thickness, the alternating magnetic layers can be made to anti-align by way of exchange coupling, as described in S.S.P. Parkin, "Systematic Variation of the Strength and Oscillation Period of Indirect Magnetic Exchange Coupling through the 3d, 4d, and 5d Transition Metals", Physical Review Letters 67, 3598(1991), so that the device is in its high resistance state. In the presence of an immobilized magnetic particle, the magnetic moments of all the ferromagnetic layers shift to a radial orientation and the resistance through the device drops. Because the moments of all layers shift from antiparallel, this embodiment is referred to as the "scissors mode". The operation of this embodiment is further shown in FIGS. 12a and 12b, which are a cross-sectional views of a magnetic sensing element 120 without and with an immobilized magnetic particle 70. (For clarity of illustration, the electrical leads and molecules of the first binding member and the molecules of the second binding member are not shown.) In the drawings, x represents the portion of the circular magnetic moment pointing into the page, and Θ represents the portion of the circular magnetic moment pointing out of the page. As depicted in FIG. 12a, in the absence of an immobilized particle, the magnetic moment F of the top soft layer 320 is clockwise and the magnetic moment G of the bottom soft layer 220 is counterclockwise. As depicted in FIG. 12b, in the presence of an immobilized particle 70 having a magnetic fringing field with a perpendicular component C and a radial component D, the magnetic moment of both the top soft layer 320 and the bottom soft layer 220 become radial, as indicated by arrows H and J. When the magnetic moments move from anti-parallel to parallel, the resistance decreases. For the measurement of resistance, this embodiment can have either a current-in-plane (CIP) configuration or a current-perpendicular to plane (CPP) configuration.

Figure 13:
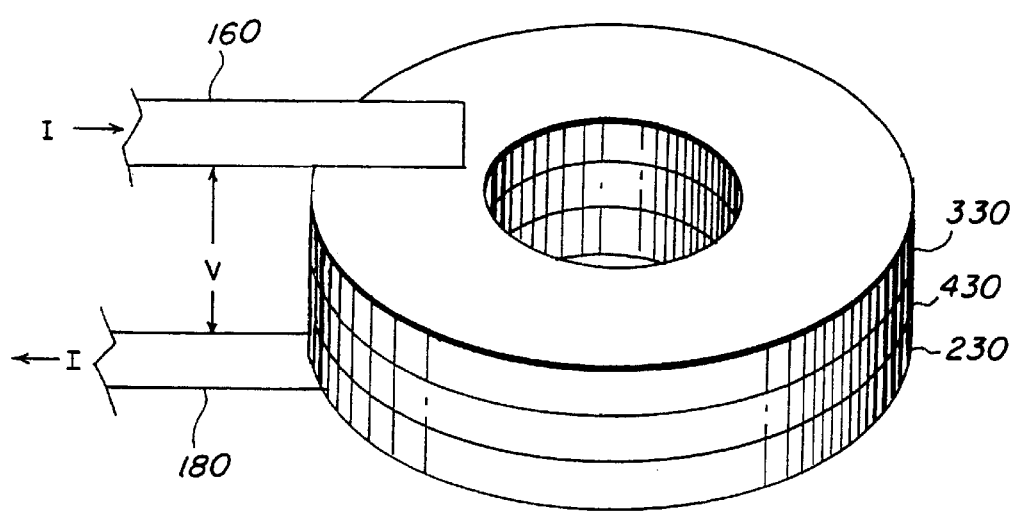
FIG. 13 is a perspective representation of a magnetic sensing element of the fourth embodiment.

A fourth embodiment, depicted in FIG. 13, is a magnetic tunnel junction (MTJ) device, that comprises two ferromagnetic layers, one hard layer 230 and one soft layer 330, separated by a non-magnetic insulator 430. (Basically, it is the same structure as the first embodiment, except that the nonferromagnetic layer is an insulator instead of a conductor. Also, as in the first embodiment, the relative position of the hard and soft layers could be reversed.). Conducting leads 160 and 180 provide current to pass through the ferromagnetic layers, perpendicular to magnetic moments in the ferromagnetic layers. (For clarity of illustration, the molecules of the first binding member and the molecules of the second binding member are not shown.) This embodiment utilizes the "half-scissors" mode as in the first embodiment. However, the magnetic tunnel junction generally provides a larger resistance change as compared to a GMR structure.

A fifth embodiment, also a magnetic tunnel junction (MTJ) device like the fourth embodiment, uses an electrical current as in the second embodiment to "latch" the device. In principle, a "switching" current could be sent down the ring to counterrotate the magnetization of the layers. Practically speaking, the large currents necessary for this would probably damage the tunnel junction. More preferable would be to use a coaxial auxiliary current lead for this purpose.

A sixth embodiment, an anisotropic magnetoresistive (AMR) device, includes one or more ferromagnetic layers and current leads that direct current through the sensing element in a circumferential current-in-plane (CCP) orientation. With no perturbing field from a magnetic particle, the magnetization of the ferromagnetic layers is either parallel or antiparallel to the current. The radial component of the fringing field of a magnetic particle causes the moments of the ferromagnetic layers to align radially and become perpendicular to the current flow. This results in an observable difference in magnetoresistance as a function of the angle between the sense current and the internal magnetization of the material. The resistance ratio $\Delta R/R$ varies as $$\frac{\Delta R}{R_0} = \alpha \cos^2 \phi \qquad (6)$$

where $\phi$ is the angle between the current and the magnetization and $\alpha$ is the AMR coefficient that generally ranges between ±0.04 depending upon the material. The resistance may either increase or decrease as the angle between the sense current and the internal magnetization of the material varies, depending on the sign of the AMR coefficient. The achievable signal from a current-in-plane magnetic sensing element according to this embodiment may be calculated as follows: The resistance of a ring device is given by $$R = \frac{2\pi}{t \ln(r_o/r_i)\sigma} \qquad (7)$$

where $\sigma$ is the electrical conductivity, $r_i$ and $r_o$ are the inner and outer radii of the ring respectively and t is the thickness of the ring. For a permalloy ring with thickness t=250 Å and $r_o/r_i$=1.5 the resistance will be approximately 3 k Ω. Therefore, for a 1.5% AMR, the change in resistance $\Delta R$ from a magnetic particle will be approximately 50Ω. A GMR-based current-in-plane device is expected to have a resistance of the same order but with $\Delta R/R$ as high as 10% or greater.

Figure 14A:
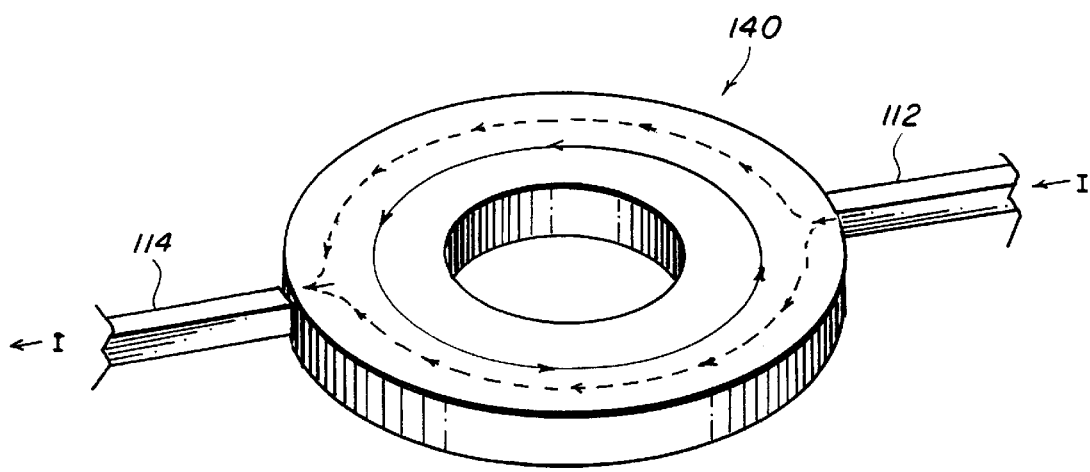
FIGS. 14a and 14b are perspective representations of a magnetic sensing element of the sixth embodiment, without and with an immobilized magnetic particle.
Figure 14B:
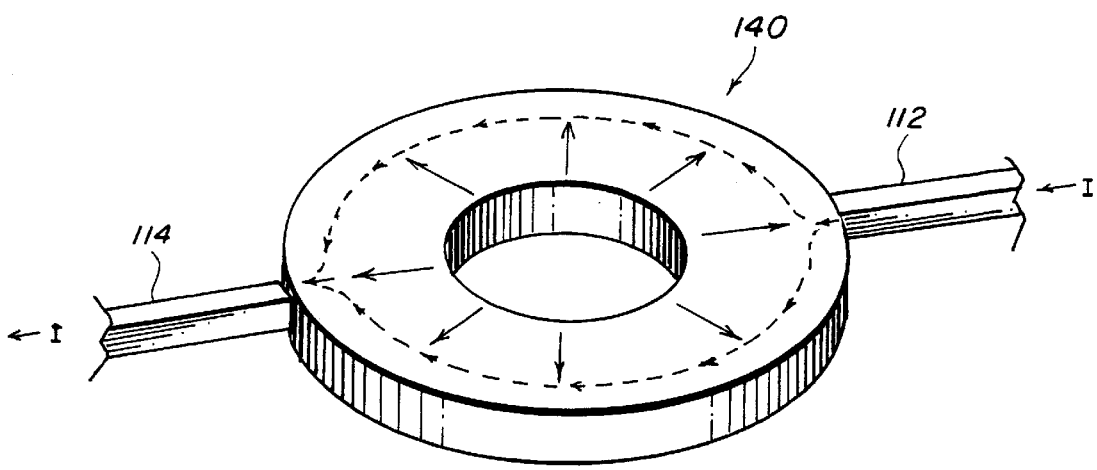

FIGS. 14a and 14b are perspective representations of an AMR-based device as described above, without and with an immobilized magnetic particle. (For clarity of illustration, molecules of the first binding member and the particle.) The magnetic sensing element comprises a ferromagnetic ring 140 that has current leads 112 and 114 that direct an electrical current I through the ring. In the absence of an immobilized particle, the ferromagnetic ring has a circular magnetic moment, as shown by arrow K. The magnetic moment is parallel or antiparallel to the flow of the current. In the presence of an immobilized magnetic particle, the magnetic moment, as shown by arrows J, becomes radial and perpendicular to the flow of the current. A measurable change in resistance is thereby created, as described above.

Sensing devices and magnetic sensing elements as described above can be readily fabricated by known methods of materials deposition, including conventional lithography. The binding members can be attached to the magnetic sensing element and to the magnetizable particles by conventional methods of attaching molecules to surfaces and particles.

Materials and dimensions of the magnetic sensing elements may typically be as described in Prinz '868. In particular, the ferromagnetic rings preferably have thicknesses of about 10 Å to about 10 Å. Preferably, the non-magnetic conductive layers and rings have thicknesses of about 10 Å to about 100 Å.

Typically, the ferromagnetic rings are Fe, Co, or Ni. Typically, the hard ferromagnetic material is selected from the alloys described in U.S. Pat. No. 4,402,770 to Koon, incorporated herein by reference. Typically, the soft magnetic material is selected from the alloys described in U.S. Pat. No. 4,402,043, to Koon, incorporated herein by reference. Typically, the ferromagnetic rings having fixed magnetic state are antiferromagnetically pinned. Typically, a hard or antiferromagnetically pinned ferromagnetic ring has a coercive field of at least 100 Oe and a softer ferromagnetic ring has a coercive field of less than 100 Oe.

Typically, an antiferromagnetic pinning layer comprises a metal oxide such as an iron oxide. Typically, the antiferromagnetic pinning layer comprises Cr or Mn, such as alloys of Cr or Mn, such as FeMn. Preferably, the ferromagnetic rings (especially soft ferromagnetic rings) are poled so that the easy axis of their magnetic moments are oriented to be either clockwise or counterclockwise with respect to the rings.

Typically, the nonferromagnetic layer comprises Cu, Au, Pt, or Ag.

Magnetic or magnetizable particles suitable for the practice of the invention are typically as described in U.S. Pat. No. 5,981,297 to Baselt. In particular, the particles may be beads or other particles made either from nanometer-sized iron oxide crystallites, polymer impregnated with nanometer-sized iron oxide crystallites, or porous glass filled with iron oxide crystallites. Such particles are commonly used for magnetic separation in molecular biology and are manufactured by several firms, including Dynal, Inc., Lake Success, N.Y.; Bangs Laboratories, Inc., Carmel, IN; CPG, Inc., Lincoln Park, N.J.; and PerSeptive Biosystems, Framingham, Mass. Typical magnetizable particles useful for binding assays range in size from approximately to 0.8 μm approximately 3 μm. These particles can be obtained with surface functional groups that can be used to immobilize molecules such as streptavidin, antibodies, or DNA. These particles behave in an essentially paramagnetic manner; that is, their magnetization is a function of the external magnetic field, and when the field is removed, the magnetization of the particles settles to zero. This "relaxation" does not happen instantly, but occurs over a period typically measured in microseconds or milliseconds. Particles fabricated from hard ferromagnetic materials (such as NdFeB), soft ferromagnetic materials (such as iron), or ferrimagnetic materials (such as micron-sized iron oxide or ferrite particles) can also be used as magnetic labels. Due to, among other things, their higher total volume of magnetic material, these three types of materials can be magnetized to a substantially greater magnetic moment than the previously described materials. However, hard ferromagnetic materials also retain their magnetism in the absence of an external magnetic field. Soft ferromagnetic and ferrimagnetic materials of spherical shape will spontaneously demagnetize in the absence of a magnetic field. These particles are preferred for the practice of the present invention over permanently magnetized particles, since magnetized particles tend to aggregate, making their use in an assay more difficult.

Figure 15:
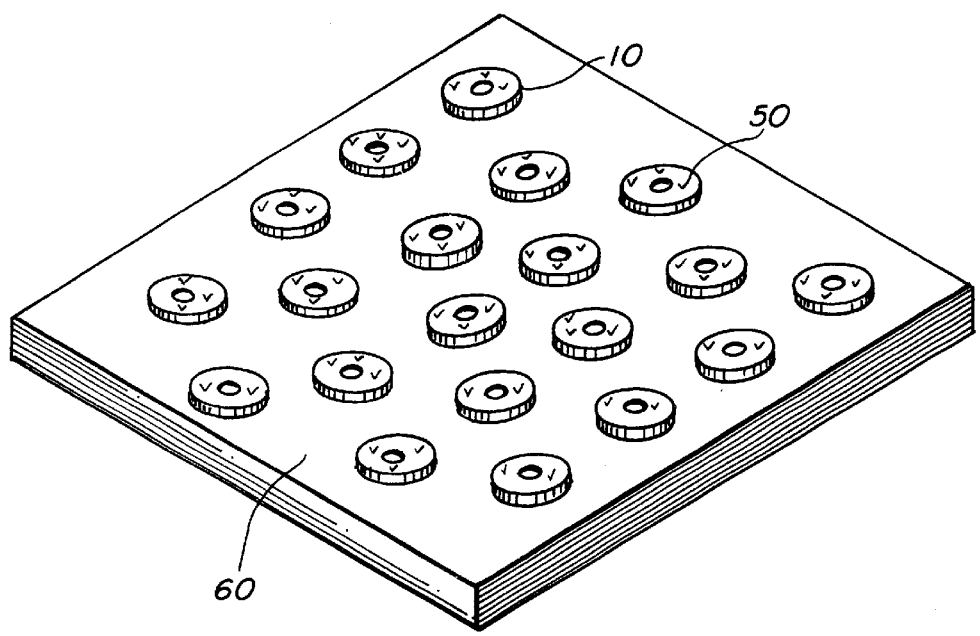
FIG. 15 is a perspective representation of an embodiment of the sensing device having an array of magnetic sensing elements, wherein each sensing element is patterned with the first binding member.

A typical assay device of the present invention, as shown in FIG. 15, comprises an array of magnetic sensing elements 10 on a solid surface 60. (For clarity of illustration, the electrical leads are not shown.) With modern microfabrication techniques, assay devices having thousands or millions of magnetic sensing elements can be constructed. As depicted in FIG. 15, each magnetic sensing element has molecules of the first binding member 15 attached to the top central portion of the element.

Figure 16:
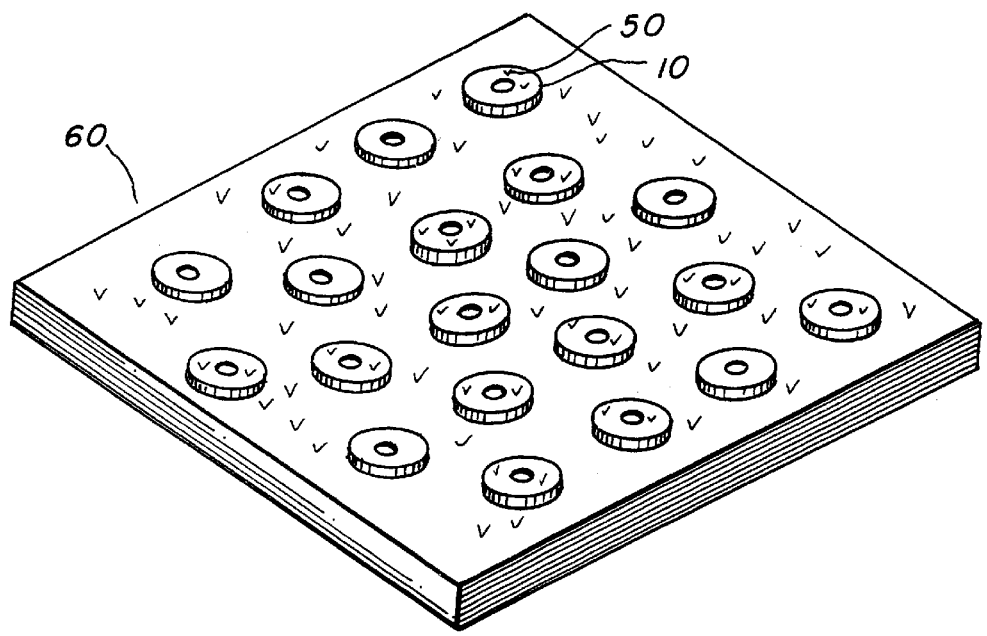
FIG. 16 is a perspective representation of an embodiment of the sensing device having an array of magnetic sensing elements, wherein entire array is randomly patterned with the first binding member.

However, to construct an array of thousands or millions of magnetic sensing elements, each having molecules of the first binding member precisely located may be prohibitively expensive. FIG. 16 depicts an alternative configuration wherein molecules of the first binding member 50 are randomly patterned over the entire area of a solid surface 60 containing the magnetic sensing elements 10. (For clarity of illustration, the electrical leads are not shown.) As a result of random patterning, some of the magnetic sensing elements will have molecules of the first binding member attached in a useful location and orientation and some will not. Detection of magnetic particles can be determined on a statistical basis. The large packing density of these sensors allows for a large filling factor (approaching 50%) of a surface, which will yield a significant fraction of beads attaching approximately on the center of many of the magnetic sensing elements. Such an implementation has the added benefit of large discrimination between beads on sensors and beads off sensors since the ring sensors will be insensitive to these off sensor beads.

Obviously, many modifications and variations of the present invention are possible in light of the above teachings. It is therefore to be understood that, within the scope of the appended claims, the invention may be practiced otherwise than as specifically described.

What is claimed is:

1. A sensing device for immobilizing and detecting the presence of a magnetic particle in a binding assay, the sensing device comprising:
   (i) a magnetic sensing element comprising at least one planar layer of electrically conductive ferromagnetic material having an initial state in which the material has a circular magnetic moment within the plane of the layer, the magnetic sensing element having molecules of a first specific binding member attached thereto, the molecules of the first binding member being selected and located so that they are capable of directly or indirectly immobilizing a magnetic particle in a binding assay in a position with respect to the planar layer such that the fringing field of the magnetic particle is able to cause the magnetic moment of at least one layer of electrically conductive ferromagnetic material to shift from circular to radial, thereby causing a detectable change in the electrical resistance of the magnetic sensing element, and
   (ii) means to detect the change in the electrical resistance of the magnetic sensing element.

2. A sensing device for detecting the presence of an analyte, the sensing device comprising:
   (i) a magnetic sensing element comprising at least one planar layer of electrically conductive ferromagnetic material having an initial state in which the material has a circular magnetic moment within the plane of the layer, the magnetic sensing element having molecules of a first specific binding member attached thereto,
   (ii) a fluid test medium including a magnetizable particle having molecules of a second specific binding member attached thereto,
      wherein the magnetizable particle has a fringing field having radial and perpendicular components,
      wherein the first specific binding member and the second specific binding member are selected so that the first specific binding member and the second specific binding member interact with each other to cause the magnetizable particle to become immobilized with respect to the magnetic sensing element in relation to the amount of the analyte in the test medium,
      wherein the relative size of the magnetizable particle and the magnetic sensing element and the location of the molecules of the first specific binding member are selected so that when the magnetizable particle becomes immobilized with respect to the magnetic sensing element, the radial fringing field of the magnetizable particle is able to cause the magnetic moment of at least one layer of electrically conductive ferromagnetic material to shift from circular to radial, thereby causing a detectable change in the electrical resistance of the magnetic sensing element, and
   (iii) means to detect the change in the electrical resistance of the magnetic sensing element.

3. The sensing device of claim 2 wherein the means to detect the change in the electrical resistance of the magnetic sensing element comprises electrical leads that are positioned to direct a current flow through the magnetic sensing element parallel to the planar layer and means to detect changes in the current flow or voltage between the electrical leads in response to the change in electrical resistance.

4. The sensing device of claim 2 wherein the means to detect the change in the electrical resistance of the magnetic sensing element comprises
   electrical leads that are positioned to direct a current flow through the magnetic sensing element perpendicular to the planar layers and through the axis of the circular magnetic moments, and
   a detector to detect changes in the current flow or voltage between the electrical leads in response to the change in electrical resistance.

5. The sensing device of claim 2
   wherein the magnetic sensing element comprises a planar layer of electrically conductive ferromagnetic material having an initial state in which the material has a circular magnetic moment within the plane of the layer,
   wherein the immobilization of the magnetizable particle with respect to the magnetic sensing causes a detectable change in the electrical resistance of the magnetic sensing element by an anisotropic magnetoresistance effect, and
   wherein the means to detect the change in the electrical resistance of the magnetic sensing element comprises electrical leads that are positioned to direct a current flow through the magnetic sensing element parallel to the planar layer and a detector to detect changes in the current flow or voltage between the electrical leads in response to the anisotropic magnetoresistance effect.

6. The sensing device of claim 2 wherein the means to detect the change in the electrical resistance of the magnetic sensing element comprises electrical leads that are positioned to direct a current flow through the magnetic sensing element parallel to the planar layer and a detector to detect changes in the current flow or voltage between the electrical leads in response to the change in electrical resistance.

7. The sensing device of claim 2 wherein the means to detect the change in the electrical resistance of the magnetic sensing element comprises
   electrical leads that are positioned to direct a current flow through the magnetic sensing element perpendicular to the planar layers and through the axis of the circular magnetic moments, and a detector to detect changes in the current flow or voltage between the electrical leads in response to the change in electrical resistance.

8. A sensing device for detecting the presence of an analyte, the sensor comprising:

a solid surface a plurality of magnetic sensing elements on the surface, each magnetic sensing element comprising at least one planar layer of electrically conductive ferromagnetic material having an initial state in which the material has a circular magnetic moment within the plane of the layer, the magnetic sensing elements having molecules of a first specific binding member attached thereto, a fluid test medium including a plurality of magnetizable particles having molecules of a second specific binding member attached thereto, wherein each magnetizable particle has a fringing field having radial and perpendicular components, wherein the first specific binding member and the second specific binding member are selected so that the first specific binding member and the second specific binding member interact with each other to cause the magnetizable particles to become immobilized with respect to the magnetic sensing elements in relation to the amount of the analyte in the test medium, wherein the relative size of the magnetizable particles and the magnetic sensing elements and the location of the molecules of the first specific binding member are selected so that when a magnetizable particle becomes immobilized with respect to a magnetic sensing element, the radial fringing field of the magnetizable particle is able to cause the magnetic moment of at least one layer of electrically conductive ferromagnetic material to shift from circular to radial, thereby causing a detectable change in the electrical resistance of the magnetic sensing element, and means to detect changes in the electrical resistance of the magnetic sensing elements.

9. A sensing device for immobilizing and detecting the presence of a magnetic particle in a binding assay, the sensing device comprising:

(i) a magnetic sensing element comprising at least one planar layer of electrically conductive ferromagnetic material having an initial state in which the material has a circular magnetic moment within the plane of the layer, the magnetic sensing element having molecules of a first specific binding member attached thereto, the molecules of the first binding member being selected and located so that they are capable of directly or indirectly immobilizing a magnetic particle in a binding assay in a position with respect to the planar layer such that the fringing field of the magnetic particle is able to cause the magnetic moment of at least one layer of electrically conductive ferromagnetic material to shift from circular to radial, thereby causing a detectable change in the electrical resistance of the magnetic sensing element, and (ii) a detector to detect the change in the electrical resistance of the magnetic sensing element.

10. The sensing device of claim 9 wherein the magnetic sensing element comprises a stack of ferromagnetic layers, said stack comprising:

a planar layer of electrically conductive, magnetically hard ferromagnetic material having a fixed circular magnetic moment within the plane of the layer, a planar layer of electrically conductive, magnetically soft ferromagnetic material having a initial state in which the material has a circular magnetic moment within the plane of the layer, wherein the layer of magnetically hard material and the layer of magnetically soft material are separated from each other by a planar layer of electrically conductive nonferromagnetic material.

11. The sensing device of claim 10 wherein, in the initial state, the circular magnetic moment of the planar layer of electrically conductive, magnetically soft ferromagnetic material is parallel to the circular magnetic moment of the planar layer of electrically conductive, magnetically hard ferromagnetic material.

12. The sensing device of claim 10 wherein, in the initial state, the circular magnetic moment of the planar layer of electrically conductive, magnetically soft ferromagnetic material is antiparallel to the circular magnetic moment of the planar layer of electrically conductive, magnetically hard ferromagnetic material.

13. The sensing device of claim 10 wherein the magnetic sensing element comprises a stack of coaxial ferromagnetic rings, said stack comprising:

a ring of electrically conductive, magnetically hard ferromagnetic material having a fixed circular magnetic moment within the plane of the layer, a ring of electrically conductive, magnetically soft ferromagnetic material having a initial state in which the material has a circular magnetic moment within the plane of the layer, wherein the ring of electrically conductive, magnetically hard ferromagnetic material and the ring of electrically conductive, magnetically hard ferromagnetic material are separated from each other by a ring of electrically conductive nonferromagnetic material, and wherein the sensing device further includes a device to reverse the orientation of the circular magnetic moment of the ring of electrically conductive, magnetically soft ferromagnetic material.

14. The sensing device of claim 13 wherein the means to reverse the orientation of the circular magnetic moment of the ring of electrically conductive, magnetically soft ferromagnetic material comprises a current-carrying wire that passes axially through the center of the rings.

15. The sensing device of claim 9 wherein the magnetic sensing element comprises a stack of ferromagnetic layers, said stack comprising:

a first planar layer of electrically conductive ferromagnetic material having a fixed circular magnetic moment within the plane of the layer, a second planar layer of electrically conductive ferromagnetic material having a initial state in which the material has a circular magnetic moment within the plane of the layer, wherein the first planar layer of electrically conductive ferromagnetic material and the second planar layer of electrically conductive ferromagnetic material are separated from each other by a planar layer of electrically conductive nonferromagnetic material, wherein the first planar layer and the second planar layer have equal magnetic coercivities and wherein the circular magnetic moments of first planar layer and the second planar layer are antiparallel.

16. The sensing device of claim 9 wherein the magnetic sensing element comprises a stack of ferromagnetic layers, said stack comprising:

a plurality of planar layers of electrically conductive, magnetically hard ferromagnetic material, each of the magnetically hard layers having a circular magnetic moment within the plane of the respective magnetically hard layer, said magnetic moments of the layers of magnetically hard material being aligned parallel with respect to each other;

a plurality of planar layers of electrically conductive, magnetically soft ferromagnetic material, each of the layers of magnetically soft material having a initial state wherein each layer has a circular magnetic moment within the plane of the respective layer of magnetically soft material and wherein the magnetic moments of the layers of magnetically soft material being aligned parallel with respect to each other, wherein layers of magnetically hard material and layers of magnetically soft material are separated from each other by electrically conductive planar layers of non-ferromagnetic material.

17. A sensing device for detecting the presence of an analyte, the sensing device comprising:

(i) a magnetic sensing element comprising at least one planar layer of electrically conductive ferromagnetic material having an initial state in which the material has a circular magnetic moment within the plane of the layer, the magnetic sensing element having molecules of a first specific binding member attached thereto, (ii) a fluid test medium including a magnetizable particle having molecules of a second specific binding member attached thereto, wherein the magnetizable particle has a fringing field having radial and perpendicular components, wherein the first specific binding member and the second specific binding member are selected so that the first specific binding member and the second specific binding member interact with each other to cause the magnetizable particle to become immobilized with respect to the magnetic sensing element in relation to the amount of the analyte in the test medium, wherein the relative size of the magnetizable particle and the magnetic sensing element and the location of the molecules of the first specific binding member are selected so that when the magnetizable particle becomes immobilized with respect to the magnetic sensing element, the radial fringing field of the magnetizable particle is able to cause the magnetic moment of at least one layer of electrically conductive ferromagnetic material to shift from circular to radial, thereby causing a detectable change in the electrical resistance of the magnetic sensing element, and (iii) a detector to detect the change in electrical resistance of the magnetic sensing element.

18. The sensing device of claim 17 wherein the magnetizable particle is a soft ferromagnetic bead.

19. The sensing device of claim 17 wherein the magnetic sensing element comprises a stack of ferromagnetic layers, said stack comprising:

a planar layer of electrically conductive, magnetically hard ferromagnetic material having a fixed circular magnetic moment within the plane of the layer, a planar layer of electrically conductive, magnetically soft ferromagnetic material having a initial state in which the material has a circular magnetic moment within the plane of the layer, wherein the layer of magnetically hard material and the layer of magnetically soft material are separated from each other by a planar layer of electrically conductive nonferromagnetic material.

20. The sensing device of claim 19 wherein the means to detect the change in the electrical resistance of the magnetic sensing element comprises electrical leads that are positioned to direct a current flow through the magnetic sensing element perpendicular to the planar layers and through the axis of the circular magnetic moments, means to detect changes in the current flow or voltage between the electrical leads in response to the change in electrical resistance.

21. The sensing device of claim 19 wherein, in the initial state of the layer of magnetically soft material, the circular magnetic moment of the layer of magnetically soft material is antiparallel with respect to the circular magnetic moment of the layer magnetically hard material.

22. The sensing device of claim 19 wherein, in the initial state of the layer of magnetically soft material, the magnetic moment of the layer of magnetically soft material is parallel to the magnetic moment of the layer magnetically hard material.

23. The sensing device of claim 17 wherein the magnetic sensing element comprises a stack of ferromagnetic layers, said stack comprising:

a first planar layer of electrically conductive, magnetically soft ferromagnetic material having a fixed circular magnetic moment within the plane of the layer, a second planar layer of electrically conductive, magnetically soft ferromagnetic material having a initial state in which the material has a circular magnetic moment within the plane of the layer, wherein the layer of magnetically hard material and the layer of magnetically soft material are separated from each other by a planar layer of electrically conductive nonferromagnetic material and wherein the circular magnetic moments of first planar layer and the second planar layer are antiparallel.

24. The sensing device of claim 17 wherein magnetic sensing element comprises a stack of ferromagnetic layers, said stack comprising:

a plurality of planar layers of electrically conductive, magnetically hard ferromagnetic material, each of the magnetically hard layers having a circular magnetic moment within the plane of the respective magnetically hard layer, said magnetic moments of the layers of magnetically hard material being aligned parallel with respect to each other;

a plurality of planar layers of electrically conductive, magnetically soft ferromagnetic material, each of the layers of magnetically soft material having a initial state wherein each layer has a circular magnetic moment within the plane of the respective layer of magnetically soft material and wherein the magnetic moments of the layers of magnetically soft material being aligned parallel with respect to each other, wherein layers of magnetically hard material and layers of magnetically soft material are separated from each other by electrically conductive planar layers of non-ferromagnetic material.

25. The sensing device of claim 24 wherein, in the unperturbed state of the layers of magnetically soft material, the magnetic moments of the layers of magnetically soft material are antiparallel with respect to the magnetic moments of the layers of magnetically hard material.

26. The sensing device of claim 24 wherein, in the initial state of the layers of magnetically soft material, the magnetic moments of the layers of magnetically soft material are parallel to the magnetic moments of the layers of magnetically hard material.

27. The sensing device of claim 17 wherein the magnetic sensing element comprises a stack of ferromagnetic layers, said stack comprising:

a first planar layer of electrically conductive ferromagnetic material having an initial state wherein the material has a circular magnetic moment within the plane of the layer, a second planar layer of electrically conductive ferromagnetic material having an initial state wherein the material has a circular magnetic moment within the plane of the layer, a planar layer of non-conductive, non-ferromagnetic material between the first planar layer of electrically conductive ferromagnetic material and the second planar layer of non-conductive ferromagnetic material, wherein the first planar layer of electrically conductive ferromagnetic material, the second planar layer of electrically conductive ferromagnetic material and the planar layer of non-conductive, non-ferromagnetic material together form a magnetic tunneling junction.

28. A sensing device for detecting the presence of an analyte, the sensor comprising:

a solid surface a plurality of magnetic sensing elements on the surface, each magnetic sensing element comprising at least one planar layer of electrically conductive ferromagnetic material having an initial state in which the material has a circular magnetic moment within the plane of the layer, the magnetic sensing elements having molecules of a first specific binding member attached thereto, a fluid test medium including a plurality of magnetizable particles having molecules of a second specific binding member attached thereto, wherein each magnetizable particle has a fringing field having radial and perpendicular components, wherein the first specific binding member and the second specific binding member are selected so that the first specific binding member and the second specific binding member interact with each other to cause the magnetizable particles to become immobilized with respect to the magnetic sensing elements in relation to the amount of the analyte in the test medium, wherein the relative size of the magnetizable particles and the magnetic sensing elements and the location of the molecules of the first specific binding member are selected so that when a magnetizable particle becomes immobilized with respect to a magnetic sensing element, the radial fringing field of the magnetizable particle is able to cause the magnetic moment of at least one layer of electrically conductive ferromagnetic material to shift from circular to radial, thereby causing a detectable change in the electrical resistance of the magnetic sensing element, and a detector to detect changes in the electrical resistance of the magnetic sensing elements.

* * * * *